(12) United States Patent
Branden et al.

(10) Patent No.: US 7,824,853 B2
(45) Date of Patent: Nov. 2, 2010

(54) COMPLEX COMPRISING AT LEAST TWO BIOSPECIFIC ELEMENTS SEPARATED BY A NUCLEIC ACID LINKER E.G. FOR IDENTIFICATION OF DRUG DELIVERY CANDIDATES COMBINATORIAL LIBRARY OF SUCH COMPLEXES

(75) Inventors: Lars Branden, Woodbridge, CT (US); Edvard Smith, Stockholm (SE)

(73) Assignee: Avaris AB, Huddinge (SE)

( * ) Notice: Subject to any disclaimer, the term of this patent is extended or adjusted under 35 U.S.C. 154(b) by 836 days.

(21) Appl. No.: 10/505,336

(22) PCT Filed: Feb. 20, 2003

(86) PCT No.: PCT/SE03/00277
§ 371 (c)(1),
(2), (4) Date: Mar. 21, 2005

(87) PCT Pub. No.: WO03/070982
PCT Pub. Date: Aug. 28, 2003

(65) Prior Publication Data
US 2005/0164191 A1     Jul. 28, 2005

(30) Foreign Application Priority Data
Feb. 22, 2002    (SE) ..................... 0200531

(51) Int. Cl.
*C12Q 1/68* (2006.01)
*G01N 33/53* (2006.01)
*C12P 19/34* (2006.01)
*C07H 21/02* (2006.01)
*C07H 21/04* (2006.01)

(52) U.S. Cl. ............ 435/6; 435/7.1; 435/91.1; 536/23.1; 536/24.3

(58) Field of Classification Search ............ 435/6, 435/7.1, 91.1, 183; 436/94, 501; 536/23.1, 536/24.3; 530/300, 350; 424/130.1
See application file for complete search history.

(56) References Cited

U.S. PATENT DOCUMENTS

| | | | |
|---|---|---|---|
| 5,451,503 A * | 9/1995 | Hogan et al. ............ 435/6 |
| 6,017,707 A | 1/2000 | Mandrand et al. |
| 6,270,964 B1 | 8/2001 | Micknick et al. |
| 6,420,532 B1 * | 7/2002 | Gerald et al. ............ 530/412 |

FOREIGN PATENT DOCUMENTS

| | | |
|---|---|---|
| WO | WO 9118117 | 11/1991 |
| WO | WO 9416108 | 7/1994 |
| WO | WO 9807845 | 2/1998 |
| WO | WO 9949293 | 8/1999 |
| WO | WO 9960169 | 11/1999 |
| WO | WO 0015824 | 3/2000 |

\* cited by examiner

*Primary Examiner*—Frank W Lu
(74) *Attorney, Agent, or Firm*—Young & Thompson (57) ABSTRACT

A method for the production of a biomolecular complex having at least two functional elements each attached to a target molecule or area through binding elements, wherein each functional element is attached to a specific binding element, the binding element being a nucleotide sequence and the target molecule or area comprising the corresponding target sequence, and the target molecules or areas being separated from each other by a first linker or spacer and an optional second linker, the linkers being nucleic acid polymers having a pre-determined physical property.

9 Claims, 3 Drawing Sheets

SEQUENCE LISTING

<160> NUMBER OF SEQ ID NOS: 8

<210> SEQ ID NO 1
<211> LENGTH: 15
<212> TYPE: DNA
<213> ORGANISM: artificial sequence
<220> FEATURE:
<223> OTHER INFORMATION: synthetic oligonucleotide

<400> SEQUENCE: 1
caatcggaac ggatc                                                      15

<210> SEQ ID NO 2
<211> LENGTH: 15
<212> TYPE: DNA
<213> ORGANISM: artificial sequence
<220> FEATURE:
<223> OTHER INFORMATION: synthetic oligonucleotide

<400> SEQUENCE: 2
ggaagggccg agcgc                                                      15

<210> SEQ ID NO 3
<211> LENGTH: 14
<212> TYPE: PRT
<213> ORGANISM: Artificial sequence
<220> FEATURE:
<223> OTHER INFORMATION: synthetic peptide

<400> SEQUENCE: 3

Gly Arg Lys Lys Arg Arg Gln Arg Arg Pro Pro Gln Cys
1               5                   10

<210> SEQ ID NO 4
<211> LENGTH: 8
<212> TYPE: PRT
<213> ORGANISM: artificial sequence
<220> FEATURE:
<223> OTHER INFORMATION: synthetic peptide

<400> SEQUENCE: 4

Lys Ala Phe Arg Ser Ala Ala Gln
1               5

<210> SEQ ID NO 5
<211> LENGTH: 10
<212> TYPE: DNA
<213> ORGANISM: artificial sequence
<220> FEATURE:
<223> OTHER INFORMATION: synthetic oligonucleotide

<400> SEQUENCE: 5
cctgtaatct                                                            10

<210> SEQ ID NO 6
<211> LENGTH: 10
<212> TYPE: DNA
<213> ORGANISM: artificial sequence
<220> FEATURE:
<223> OTHER INFORMATION: synthetic oligonucleotide

<400> SEQUENCE: 6
ggacattaga                                                            10

```
<210> SEQ ID NO 7
<211> LENGTH: 10
<212> TYPE: DNA
<213> ORGANISM: artificial sequence
<220> FEATURE:
<223> OTHER INFORMATION: synthetic oligonucleotide

<400> SEQUENCE: 7
gcatctctag                                                          10

<210> SEQ ID NO 8
<211> LENGTH: 10
<212> TYPE: DNA
<213> ORGANISM: artificial sequence
<220> FEATURE:
<223> OTHER INFORMATION: synthetic oligonucleotide

<400> SEQUENCE: 8
cgtagagatc                                                          10
```

COMPLEX COMPRISING AT LEAST TWO BIOSPECIFIC ELEMENTS SEPARATED BY A NUCLEIC ACID LINKER E.G. FOR IDENTIFICATION OF DRUG DELIVERY CANDIDATES COMBINATORIAL LIBRARY OF SUCH COMPLEXES

The present invention concerns biomolecular complexes and in particular a method for linking biomolecules in sets of two or more, with predefined three-dimensional orientation and spacing between said at least two biomolecules. Said linking method has application in the construction of novel, highly specific vehicles or vectors for drug delivery, for example in gene therapy, and in the construction and performing of assays for the study of biomolecular interaction, such as protein-protein, and especially receptor-ligand, interaction studies.

BACKGROUND OF THE INVENTION

Drug target discovery today is to a large extent based on the design of individual effector molecules on the basis of known target structures. Modern drug design is also based on single receptor-ligand interactions. In nature this is often not the case, as is exemplified by many viruses, which interact with more than one receptor. HIT has been shown to bind to both CD4 and chemokine receptors such as CCR5, and adenoviruses have been shown to bind both to integrins and to the CAR-protein. In addition to these, additional receptors have recently been identified. It seems likely that this concept is general and that efficient uptake of particles, such as viruses, is caused by the combined interaction with two or possibly more receptors. It is known from the study of adenoviruses that one of the constraints in viral particle uptake is the positioning of the ligands for integrins and for CAR. Thus the shafts or antennae of the adenoviral particle need to be of a certain length in order for internalisation. For most two-receptor systems, very little is however known about the optimal distances between the ligands, their orientation and exact mechanisms of interaction.

PRIOR ART

WO 91/18117 is an application directed to methods for detecting the presence or determining the concentration of a particular sequence, wherein different probes are used to identify, said sequence, bind to it and to aid in the subsequent separation and/or detection thereof.

WO 94/16108 discloses a nucleic acid sandwich hybridisation assay to detect the presence in a sample of a preselected nucleic acid target containing a target sequence.

WO 99/60169 lists numerous examples of multimolecular devices without any credible reduction to practice. In a speculative and non-specific manner, numerous practical applications are given, again without scientific or technical support.

U.S. Pat. No. 6,017,707 concerns methods for the detection of a nucleotide sequence of interest and discloses a probe marked with a tracer, and a reagent comprising a linear backbone having lateral substituents. One of said substituents is capable of hybridising to said sequence of interest, while the other hybridises to the probe. Such a reagent enables signal amplification and lowers the sensitivity threshold.

WO 00/15824 describes a transfer method for specific cellular localisation of nucleic acids. The method is based on the use of peptide nucleic acids (PNA) as binding elements on a carrier molecule, and functional elements coupled to said binding elements. According to WO 00/15824, the functional element/-s may be separated from the binding element/-s by a linker. The carrier molecule may also comprise one or more detectable marker elements, or labels, such as labels detectable by spectroscopic, photochemical, biochemical, immunological or chemical means.

WO 00/15824 discloses a transport entity, e.g. for the transport of nucleic acids over biological membranes, said transport entity comprising two or more functional elements, preferably spaced by linkers. A linker, according to WO 00/15824, may be comprised of a polymer of a suitable number of amino acid residues, or any other suitable molecule which functions as a spacer element without interfering with the desired function of the functional elements. Using the transport entity according to WO 00/15824, is possible to mimic the different functions of viruses and microorganisms by attaching functions directly to a nucleic acid or any other biological molecule and/or complex to be transferred to a cell.

It is the aim of the present inventors to develop this concept further. In the light of the available prior art, there remains the need for a simple, fast, and flexible but at the same time reliable method for the production of biochemical complexes.

One aim of the present invention is to make available a practical method for the production of biomolecular complexes with pre-determined and well-defined three-dimensional orientation and/or spacing between the biomolecules involved.

Another aim is to establish a method for identifying receptor combinations that will provide improved or optimal uptake of drugs, and to construct vectors for drugs delivery, including vectors for gene delivery.

Another aim is to make available a method and technology for receptor screening, and in particular for high throughput combinatorial receptor screening.

Another aim is to make available means and methods for the study of biomolecular interaction, such as protein-protein interaction studies, and especially receptor-ligand interaction studies.

It is also an aim of the invention to study and to improve the binding and uptake of substances through biological membranes, for example so called internalisation, both extra—and intracellular binding and uptake, using specific binding mechanisms.

Further aims and objectives, met by the present invention, and the advantages associated therewith, will become evident to a skilled person upon study of the description and examples.

SUMMARY OF THE INVENTION

The present invention makes available a biomolecular complex comprising at least two functional elements each attached to a target molecule or area through binding elements, wherein each functional element is attached to a specific binding element, said binding element being a nucleotide sequence and the target molecule or area comprising the corresponding target sequence, and the target molecules or areas being separated from each other by a first linker or spacer being a nucleic acid polymer.

The invention also makes available methods for the production of such complexes, as well as methods involving their use.

The inventive complex and methods are further defined in the attached claims, incorporated herein by reference.

The present invention as defined in the attached claims fulfils the above objectives and aims, and makes it possible to produce novel biomolecular complexes, by linking multiple receptor ligands in a well-defined waif and screen for cell specific uptake of the targeted molecule.

SHORT DESCRIPTION OF THE DRAWINGS

The invention will be disclosed in further detail in the following description, non-limiting examples and attached drawings, in which.

DESCRIPTION

In the present description and claims, the following terms and abbreviations will be used:

"Complementary" in the context of this description refers to the capacity for precise pairing between two sequences, such as two nucleotide sequences.

Further, in the context of the present invention, "hybridisation" refers to hydrogen bonding, which may be Watson-Crick, Hoogsteen or reverse Hoogsteen hydrogen bonding, between complementary nucleoside or nucleotide bases. Thus complementarity and hybridisation are terms used to indicate a sufficient degree of complementarity or precise paring such that stable and specific binding occurs between the oligonucleotide and the DNA or RNA target.

For example an antisense compound is specifically hybridisable when binding of the compound to the target DNA or RNA molecule interferes with the normal function of the target DNA or RNA to cause a loss of utility, and there is a sufficient degree of complementarity to avoid non-specific binding of the antisense compound to non-specific target sequences under conditions in which specific binding is desired.

The phrase "hybridisation under stringent conditions" refers to criteria regarding temperature and buffers well known to those skilled in the art. See e.g. Sambrook, J., Fritsch, E. F. and Maniatis. T., Molecular cloning: A laboratory manual, 2nd Edition. Cold Spring Harbour Laboratory Press, USA (1989).

In the following description, the term "functional element" (FE) will be used to denote any moiety capable of conferring one or more specific biological functions or properties to a molecule linked to it. Functional elements of interest in the present invention are for example peptides, lipids, glycoproteins, and preferably receptor ligands and fractions thereof, including both natural and synthetic peptides, lipids, glycoproteins and ligands.

A "binding element" (BE) may be any natural or synthetic nucleic acid, nucleic acid derivative or nucleic acid analogue capable of specific, strong and durable binding to a specified target thereof, preferably by hybridisation. One example of such BE is the PNA described below.

A "target" or "target region" is a specific region corresponding to a BE, and may be any natural or synthetic nucleic acid, nucleic acid derivative or nucleic acid analogue capable of specific, strong and durable binding to a specified BE preferably by hybridisation. Preferably the desired targets or target regions are synthesised integrated in a nucleotide sequence, where the non-target sequence portion or portions function as a linker. For example, the target regions may be positioned at each end of a nucleotide sequence, while the middle portion of said sequence forms a linker of predetermined length and orientation.

The target regions may also be adjacent or substantially adjacent regions, distributed locally or over the entire length of the nucleotide sequence, thus making it possible to produce a multimer or a complex having multiple functional entities, said entities being the same or different.

A "linker" (L, l) may be any chemical stricture connecting two BEs or an FE and a BE, defining a distance and orientation between these. Preferably a linker does not participate in the chemical/biochemical interactions of the FEs. The linker is preferably a nucleic acid polymer, such as a single stranded or double stranded nucleic acid polymer, and most preferably a single stranded polymer. However, when using binding elements synthesised from PNA, double stranded nucleic acid polymers can be used.

"PNA" is an acronym for Peptide Nucleic Acid, which is a DNA mimic having a pseudopeptide backbone consisting of aminoethyl glycine units, to which the nucleobases are attached via methylen carbonyl linkers. A PNA molecule is capable of hybridising to complementary ssDNA, dsDNA, RNA and PNA targets. In the present application, it is to be understood that the term "PNA" refers to any DNA analogue comprising a suitable backbone and nucleobases, and the term is thus not limited to the specific structures disclosed herein.

A "label" or "marker" is a composition detectable by spectroscopic, photochemical, biochemical, radioactive, immunological or chemical means. One example of suitable labels are commercially available fluorescent markers, such as fluorophores. There are at least two types of fluorophores: conjugates and probes. A conjugate is a fluorophore that is usually attached to a ligand such as an antibody (e.g. Alexa Fluors®, Cy®, Bodipy® dyes). A fluorescent probe is a fluorophore designed to localise within a specific region of a cell or to respond to a specific stimulus (e.g pH indicators, XFP's, DAPI). Also radioactive markers and other commercially available marker substances can be used.

The present invention makes a contribution over the prior art in that it makes available a novel complex and method for its production and use. The transport entity according to WO 00/15824 can be exemplified as $$\ldots BE\text{-}L\text{-}FE \ldots \quad (1)$$

wherein BE denotes a binding element, L denotes a linker (optional), and FE denotes a functional element.

The biomolecular complex according to the present invention, differs from the transport entity in that the position/orientation and/or distance between two or more functional elements is accurately controlled. The complex according to the invention can be illustrated as $$FE_1\text{-}BE_1\text{-}T_1\text{-}L\text{-}T_2\text{-}BE_2\text{-}FE_2 \quad (2)$$

wherein $T_1$ and $T_2$ denote target areas; L is a linker or spacer of predetermined length, or other specific quality; $BE_1$ and $BE_2$ denote binding elements; and $FE_1$ and $FE_2$ denote functional elements. The linker is optionally a rigid linker, depending on the intended use of biomolecular complex.

Each of the functional elements $FE_1$ and $FE_2$, the binding elements $BE_1$ and $BE_2$, and the corresponding target areas $T_1$ and $T_2$ form sub-units, each presenting one functional element. Optionally, $FE_1$ and $BE_1$, or $FE_2$ and $BE_2$ may be separated by secondary linkers (l), further determining the distance and orientation of the functional entities:

$$FE_1\text{-}l\text{-}BE_1\text{-}T_1\text{-}L\text{-}T_2\text{-}BE_2\text{-}l\text{-}FE_2 \qquad (3)$$

When the biomolecular complex comprises more than two functional elements, these are attached to binding elements corresponding to specific targets or parts of targets, optionally separated by further linkers/spacers. This complex can be illustrated by $$[(FE_x\text{-}l\text{-}BE_x)\text{-}T_x]_n\text{-}L_m \qquad (4)$$

wherein n and m are integers, and where m may be equal to n, but frequently is equal to n−1. The subscript x means that the functional entities and binding entities may, be characterised by different functionalities or binding properties, respectively.

An embodiment of the present invention is a biomolecular complex comprising, at least two functional elements ($FE_1$, $FE_2$ etc.) attached to target areas (T) through binding elements (BE), wherein each FE is attached to a specific BE, said BE exhibiting selectivity for a specific target molecule/target area or a part thereof, and the target molecules/target areas being separated from each other by a linker having a predetermined physical property.

Another embodiment is a biomolecular multimer complex, where multiple copies of the same functional element. e.g. a ligand, are coupled to binding elements, and attached through these binding elements to multiple target molecules/target areas connected by linkers, e.g. a sequence comprising multiple target areas separated by sequence portions functioning as linkers.

According to the invention, the linker can be any suitable molecule, for example a polymer having specific physical properties and which does not interfere with action of the functional elements, other than their orientation and mutual distance. The physical property of the linker is one chosen among: length, charge, secondary structure, tertiary structure, hydrophilicity, or a combination thereof. Preferably said linker is a nucleotide sequence.

According to one embodiment, the target molecule/target area comprises a marker, such as a reporter gene, or a label, such as a radioactive label or a fluorescent label.

According to one embodiment, the BE is a PNA sequence and the target molecule/target area comprises the corresponding PNA target.

One embodiment of the present invention is a method for the production of biomolecular complexes, comprising the steps of a) forming a stock solution of a first functional entity,
b) forming a stock solution of a second functional entity,
c) forming separate stock solutions of at least two binding entities,
d) forming separate stock solutions of nucleic acid molecules as linker molecules, each solution containing a linker molecule having a distinct physical property,
e) reacting said first functional entity with at least one binding entity,
f) reacting said second functional entity with at least one binding entity, other than the binding entity in e)
g) repeating steps e) and f) for each functional entity,
h) reacting each linker molecule with at least two target molecules/target areas, capable of specific binding to the binding entities of e) and f)
i) reacting each combination of functional entity and binding entity with each linker, and
j) repeating step h) in order to form a library of combinations of functional entities and linkers.

Another embodiment of the present invention is a method for the production of biomolecular complexes, comprising the steps of i) synthesis of a molecular combination of a first functional entity and a first binding entity,
ii) synthesis of a molecular combination of said first functional entity and a second binding entity,
iii) synthesis of a molecular combination of a second functional entity and said first binding entity,
iv) synthesis of a molecular combination of a second functional emir and said second binding entity, optionally repeating steps i)-iv) for further functional entities and binding entities and forming stock solutions thereof,
v) synthesis of a nucleic acid molecule as a linker connecting a fist and second target area,
vi) self-assembly of the molecular combinations of any, one of step i)-iv) to the linker of step v) in the desired configuration by, addition of these to said linker in solution.

Using the above method for producing biomolecular complexes, a combinatorial library is established, the library consisting of separate stock solutions of each functional entity coupled to its binding entity, and stock solutions of one or more linker or linkers having target areas corresponding to said binding entities. The combinatorial library may also consist of the various complexes, created when the functional entities are coupled to the linkers through the interaction between binding element and target area. One embodiment is therefore a combinatorial library, wherein the functional entities are chosen among receptor molecules, ligands for receptor molecules, or sub-units thereof, for example peptides, lipids, glycoproteins, and preferably receptor ligands and fractions thereof, including both natural and synthetic peptides, lipids, glycoproteins and ligands. Example 1 illustrates this embodiment.

One further embodiment of the present invention is a method for the screening of receptors with respect to their involvement in the internalisation of substances in eukaryote cells, and in particular a combinatorial method, wherein complexes presenting different functional entities are produced according to the method outlined above, and subjected to analysis as outlined in the attached example. As functional elements, different moieties or ligands presumed to interact with said receptors are used, and their orientation, distance and presentation to the cell is varied by appropriate choice of linkers/spacers in the inventive complex.

One further embodiment of the present invention is a method for the screening of receptors with respect to their involvement in the internalisation of substances in prokaryote cells, and in particular a combinatorial method according to the above.

Conversely, cells can be screened or selected with respect to their susceptibility to different constructs produced according to the invention. This makes it possible to differentiate between and study cells, depending on their binding patterns and/or internalisation behaviour with regard to various substances, presented on a construct according to the invention.

Another embodiment is a method for the study of intermolecular interactions under physiological or near-physiological conditions, wherein the molecule/-s of interest is/are inserted as one, two or more FEs, using a range of linkers varying the distance and orientation of the molecules in relation to each other. Example 2 illustrates this embodiment.

According to one embodiment of the invention, single molecules such as ligands, can be broken down to separate peptides and the role and function of these peptides investigated by incorporating these peptides as functional entities in a biomolecular complex according to the invention. It can in this way be elucidated which part/parts of a ligand is involved in the interaction under investigation.

The complex according to the invention in a surprising and highly advantageous way uses nucleic acids as building blocks for binding, and positioning in relation to each other, two or more functional elements, and thus makes it possible to construct novel biomolecules having both a desired structure and desired functionality in a controlled fashion. Example 3, where two different complexes were tested in vivo, serves as an illustration of this embodiment.

A complex according to the invention need not only be used in the study of molecular interaction, e.g. membrane penetration and internalisation, but can also be used as a carrier for pharmaceutical compounds. Example 4 clearly demonstrates how a construct carrying a combination of two functional entities exhibits more efficient binding to a particular cell type than constructs carrying each of these entities alone.

Consequently, the present invention also encompasses specific drug delivery vectors produced using the inventive method, as well as drug candidates identified using the method according to the invention.

The inventive method makes possible the rational and easy manufacture of combinatorial libraries, consisting of large numbers of functional entities, for example peptides, lipids, glycoproteins, and preferably receptor ligands and fractions thereof, including both natural and synthetic peptides, lipids, glycoproteins and ligands, combined in pairs, three, four or more, and connected by linkers and spacers having pre-determined physical properties.

The method according to the present invention has a significant advantage in that it makes possible the "self-assembly" of complex biomolecular structures.

The method according to the invention has the advantages of being based on relatively simple chemistry, making it possible to implement without large investments in production equipment and facilities.

Further, the method according to the present invention has a considerable advantage in that no special buffers are needed, instead the reactions can be performed under physiological or substantially physiological conditions. Further, no immobilisation is necessary when using the complexes, making the conditions of the reactions more similar to physiological conditions.

The method according to the present invention makes it possible to test different functional groups in different configurations, as the assembly of complexes having the desired spatial and functional parameters becomes easy.

EXAMPLES

Example 1

An Experimental High Through-put Screening (HTS) Set-up

Initially, for the peptides to be screened (PNA-FE$_{1-n}$ or) matching target DNA, either plasmids or oligonucleotides, are synthesised carrying the PNA target sites. For this purpose, the Qiagen automation system (Qiagen Inc., USA) may be adapted for sequential hybridisation. The oligonucleotides are further provided with a suitable marker, preferably a fluorescent label.

Each hybridisation is then deposited in a well in a 96-well plate and heat-sealed. Again, equipment e.g. from Quiagen Inc. is available, having a robotic link system that can penetrate the heat-sealed well and then apply the sample to a predetermined well in a thin-bottomed 96-well plate with cell-cultures for further incubation.

Cellomics Inc. (Pittsburgh, Pa., USA) manufactures a system for high-throughput screening of fluorescence in cells (Arrayscan II). The system can handle up to 20 96-well plates at each time. The system can control the culture conditions of the cells (temperature and $CO_2$) thus allowing for possible in vivo screening of the cells both of direct fluorescence detection of labeled nucleic acids and of GFP as a reporter for gene expression.

The Arrayscan II system is then used to incubate and screen the plates prepared as above.

Having established a library of peptides, or other functional entities of interest, linked to different PNA binding entities, these can be combined with each other on a polynucleotide linker and varied with respect to number, position, orientation, mutual distance etc.

These complexes are then brought in contact with, for example, different cell types in order to identify which combination of functional entities results in the highest binding efficiency. The results can be used to identify suitable vehicles or vectors for drug delivery to a certain cell type etc.

Example 2

Trans-phosphorylation of Btk (Bruton's Tyrosine Kinase)

Figure 1:
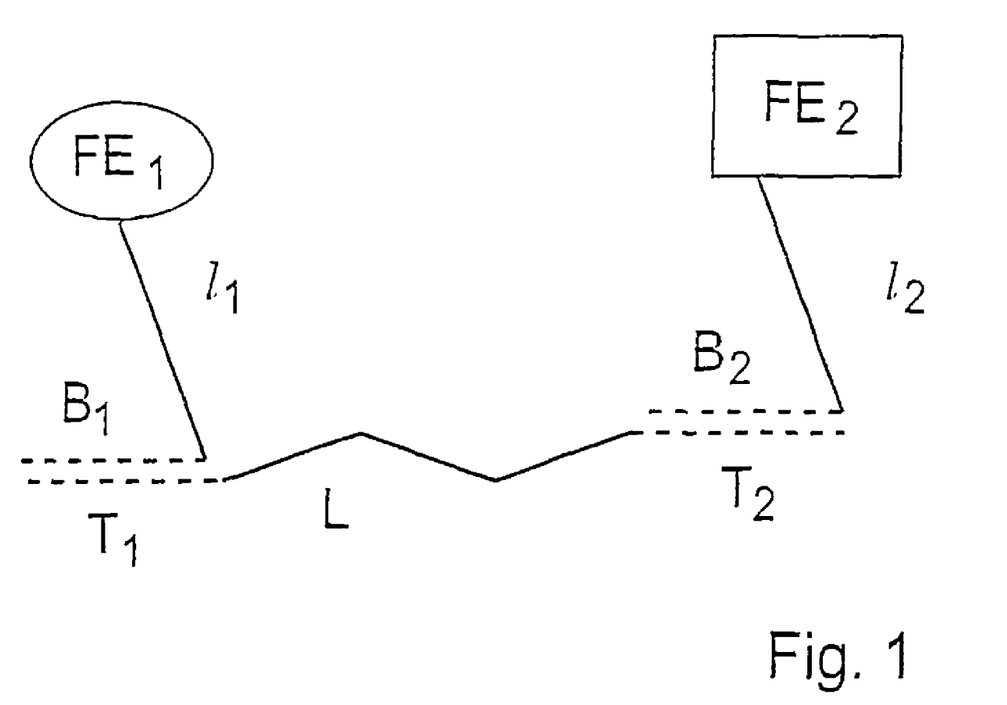
FIG. 1 shows schematically two biomolecules or functional entities, $FE_1$ and $FE_2$, connected to target areas $T_1$ and $T_2$ through binding elements $BE_1$ and $BE_2$. The distance between the functional entities and/or their orientation is determined by the rigid linker L and the optional linkers $l_1$ and $l_2$. The linker L may further comprise a marker (not shown).
Figure 2:
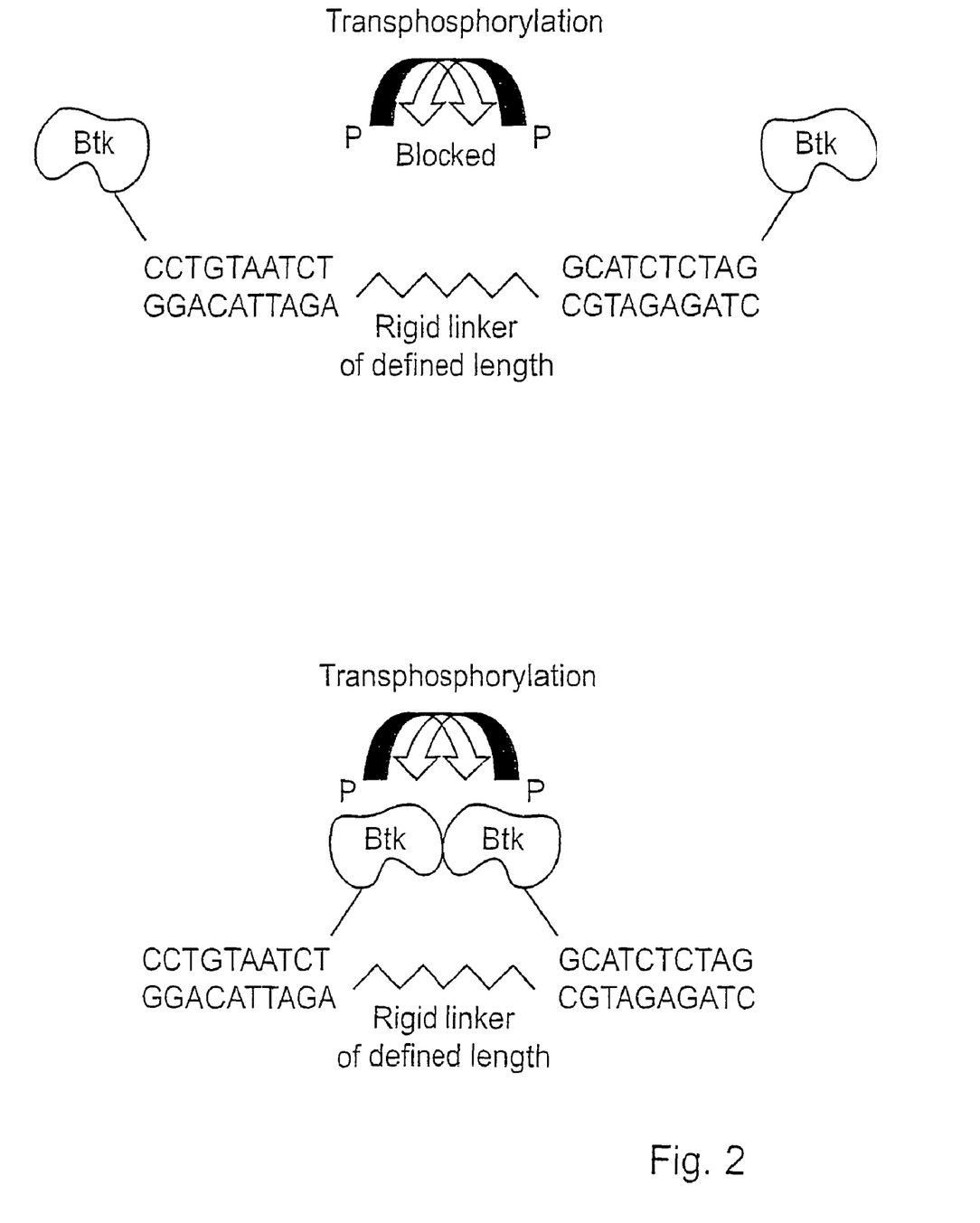
FIG. 2 shows schematically an experimental set-up, used to investigate the hypothesised trans-phosphorylation of Btk (Bruton's Tyrosine Kinase). In both the top and bottom depictions, the top left sequence is SEQ ID NO: 5, the bottom left sequence is SEQ ID NO: 6, the top right sequence is SEQ ID NO: 7, and the bottom right sequence is SEQ ID NO: 8.

The hypothesised trans-phosphorylation of Btk (Bruton's Tyrosine Kinase) is investigated using a method of constructing biomolecular complexes according to the present invention. The Btk protein is attached to a binding element via a linker (l), having a second linker (L) of defined length, for example a nucleotide sequence, joining two target areas T for connection to the binding elements. By varying the length the nucleic acid sequence constituting the second linker, as well as the orientation of the target areas, and the possible linkers between the target area and the protein, the spatial relationship between two protein molecules can be varied in order to elucidate the exact protein—protein interactions. See FIG. 2. This set-up is used to determine whether Btk can autophosphorylate or transphosphorylate itself.

Example 3

Demonstration of the Differential Effect of Receptor Interaction with a Single Functional Entity as Compared to Multiple Copies of the Same Functional Entity Oligonucleotides (60-mers) with 4 target sites (CAATCG-GAACGGATC Seq. Id. No. 1) for FE1 peptide-nucleic-acid-linker$_3$-arginine-glycine-aspartic acid (RGD) fusions and carrying different fluorescent markers (Cy-3 or Cy-5) were synthesised and hybridised to the peptide-nucleic-acidlinker$_3$-arginine-glycine-aspartic acid (RGD) fusion peptide or an inverted variant, peptide-nucleic-acid-linker$_3$-aspartic acid-glycine-arginine (DGR) fusion peptide.

Figure 3:
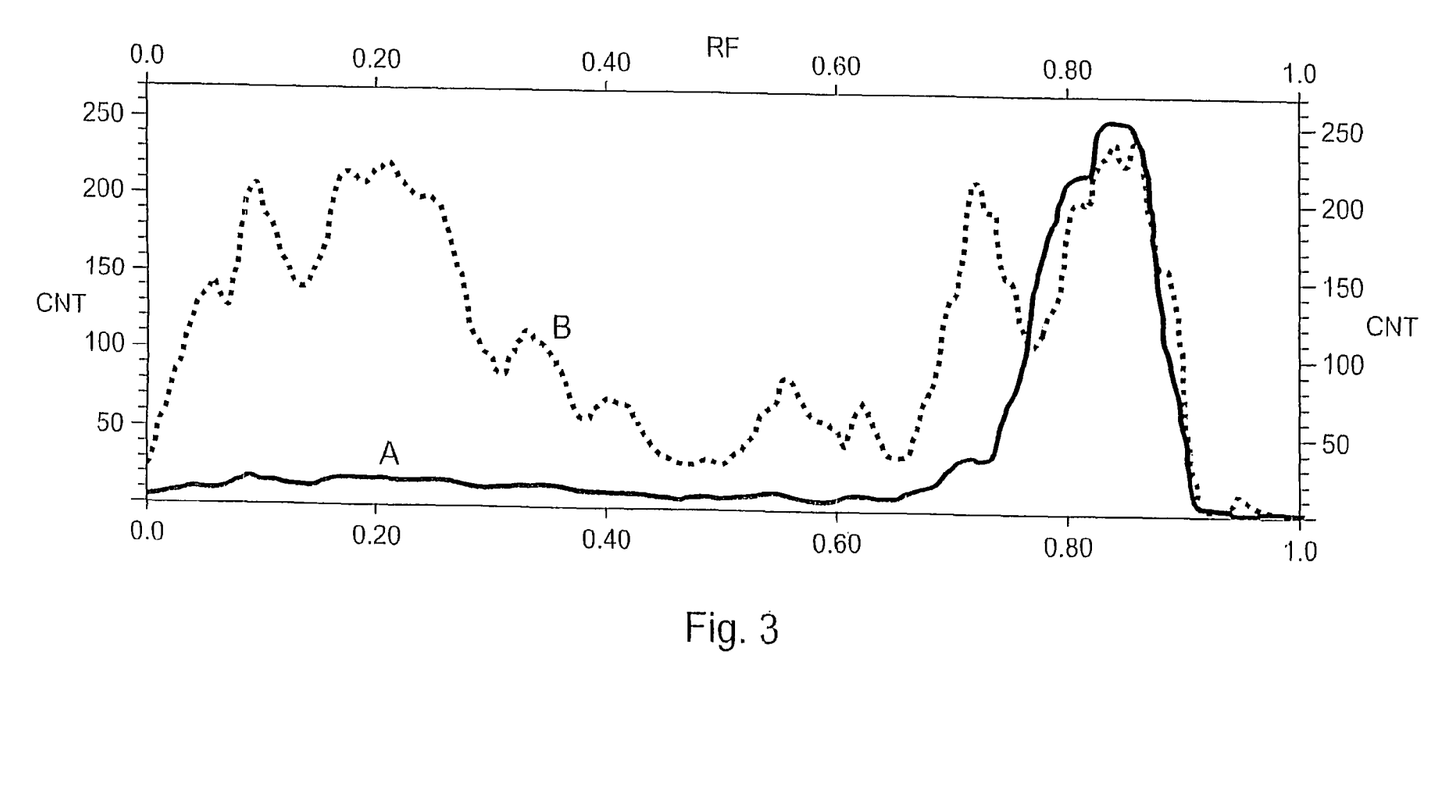
FIG. 3 is a graph showing the differential effect in vivo of receptor interaction with a single FE (FE1) as compared to multiple copies of the same FE (FE1).

Subsequently these biomolecular complexes were co-injected into mice and the tissue distribution was studied. Whole animal tissue sections were generated and the distribution of the oligonucleotides was determined. As can be seen in FIG. 3, two different patterns were observed. The curve denoted "A" corresponds to a straight line positioned across the section measuring the fluorescence from an oligonucleotide with an inverted (DGR) peptide, whereas the curve marked "B" corresponds to the same line in the same section, but instead measuring the fluorescence from the oligonucleotide hybridising to 4 peptide-nucleic-acid-linker$_3$-arginine-glycine-aspartic acid (RGD) fusion peptides.

The curves overlap partially with a peak around 0.85. This corresponds to the location of the kidney, where oligonucleotides are known to accumulate prior to secretion. The peak of the curve "B" which corresponds to the RGD-binding oligonucleotide, in the region between 0.05 and 0.25 demonstrates differences in the tissue distribution between the two different biomolecular complexes. Similar experiments carried out with non-hybridised oligonucleotides, or with oligonucleotides with a single (instead of 4) RGD binding sites gave similar results as oligonucleotides hybridised to 4 peptide-nucleic-acid-linker$_3$-arginine-glycine-aspartic acid (DGR) fusion peptides.

These findings support the concept that the novel biomolecular complexes can be used to identify receptors, which mediate specific binding and which discriminate between binding through single versus multiple ligands of the same origin.

Example 4

Monocyte Binding Assay—Demonstration of the Interaction Between Different Ligand Combinations Hybridised to Oligonucleotides Oligonucleotides (48-mers) with recognition sites for 2 different peptide-nucleic-acid sequences and with a fluorescent label were designed and manufactured. Each binding site corresponds to 15 nucleotides. The 48-mer oligos contain in the 5' end the fluorescent label, 6-FAM, followed by three thymidine residues as spacer. There is a single central target site (GGAAGGGCCGAGCGC, Seq. Id. No. 2) surrounded by two identical adjacent target sites (CAATCGGAACGGATC, Seq. Id. No. 1).

Peptide-nucleic-acid-linker$_3$-peptide (=ligand) fusions were generated as described before (Brandén L J, Mohamed A J, Smith C I E. A peptide nucleic acid-nuclear localisation signal fusion that mediates nuclear transport of DNA. *Nature Biotechnol* 17: 784-787, 1999). The following functional entities were tested: The trimer amino-acid, arginine-glycine-aspartic acid (rgd, using the single letter code for amino acid residues, FE1, also designated RGD), the Human immunodeficiency virus (HIV) peptide TAT (grkkrrqrrrppqc, (SEQ ID NO: 3) FE2) and the peptide "BULKY", which is a branched peptide with the following sequence 8*kafrsaaq (SEQ ID NO: 4) (FE3 and FE4), where 8* indicates branched lysines, the first residues following the lysine (k) being 2 lysines, followed by 4 lysines and 8 lysine residues in the end. The branched peptide was either untreated (designated charged, FE3) or acetylated (designated uncharged, FE4) to reduce the charge from the lysine residues. The TAT peptide-nucleic-acid-linker$_3$-peptide (=ligand) fusion hybridised specifically to the target site, Seq. Id. No. 2, whereas all the other constructs hybridised to the two peripheral target sites, Seq. Id. No. 1.

Peptide-nucleic-acid-linker$_3$-peptide (=ligand) fusions were hybridised to oligonucleotides in order to generate the novel biomolecular complexes. These complexes were incubated with peripheral blood mononuclear cells for one hour at +37° C., followed by trypsinisation to remove non-specific binding in order to measure binding and uptake. Following the incubation cells were analysed in a fluorescent activated cell sorter (FACS SCAN, Becton Dickinson, Mountain View, Calif.). The population, which has the characteristics of monocytes, was analysed and the results are presented in Table 1.

TABLE 1

Interaction between combinations of ligands (FE1, FE2, FE3, FE4) hybridised to oligonucleotides

| Construct(s) | Percentage of fluorescent cells |
| --- | --- |
| Untreated cells | 0.45 |
| Oligo | 1.59 |
| RGD (FE1) | 1.63 |
| TAT (FE2) | 0.93 |
| BULKY charged (FE3) | 0.88 |
| BULKY uncharged (FE4) | 1.22 |
| RGD + TAT (FE1 + FE2) | 4.68 |
| BULKY charged + TAT (FE3 + FE2) | 7.33 |
| BULKY uncharged + TAT (FE4 + FE2) | 5.49 |

As can be seen from the Table, the oligonucleotide itself (control) bound to 1.59% of all cells in the monocytic population. Surprisingly, as also can be seen from the Table, RGD (FE1) in combination with TAT (FE2); BULKY charged (FE3) in combination with TAT; and BULKY uncharged (FE4) in combination with TAT, all resulted in significantly stronger binding to cells as compared to the same functional entities (RGD, TAT, BULKY uncharged and BULKY charged) added in a singular fashion. RGD and TAT peptides, are known to interact with certain cellular structures, whereas the two BULKY peptides are novel peptides, and to the knowledge of the present inventors not previously tested for binding to cell surfaces.

These findings clearly support the concept that the biomolecular complexes according to the invention can be used to identify receptor combinations enhancing binding to cells. The findings also indicate that methods as disclosed in the present application are feasible and likely to shed light on mechanisms previously not possible to study.

Although the invention has been described with regard to its preferred embodiments, which constitute the best mode presently known to the inventors, it should be understood that various chances and modifications as would be obvious to one having the ordinary skill in this art mall be made without departing from the scope of the invention which is set forth in the claims appended hereto.

The invention claimed is:

1. A method for the production of a biomolecular complex, said method comprising the steps of:
   i) reacting a first functional element ($FE_1$) with a first binding element ($BE_1$), $BE_1$ comprising a nucleotide sequence that binds to a first target molecule or area ($T_1$), and forming a stock solution $FE_1$-$BE_1$,
   ii) reacting $FE_1$ with a second binding element ($BE_2$), BE2 comprising a nucleotide sequence that binds to a second target molecule or area ($T_2$), and forming a stock solution $FE_1$-$BE_2$,
   iii) reacting a second functional element ($FE_2$) with $BE_1$, and forming a stock solution $FE_2$-$BE_1$,
   iv) reacting $FE_2$ with $BE_2$, and forming a stock solution $FE_2$-$BE_2$,
   v) reacting a first linker molecule (L) with $T_1$ and $T_2$ and forming $T_1$-L-$T_2$, L being a nucleic acid and having a pre-determined physical property, and
   vi) reacting the stock solution of step i) and the stock solution of step iv), or the stock solution of step ii) and the stock solution of step iii), with $T_1$-L-$T_2$ and producing said biomolecular complex wherein said biomolecular complex is and, in said biomolecular complex, each of $FE_1$ and $FE_2$ is attached to one of $BE_1$ and $BE_2$, $BE_1$ is bound to $T_1$ and BE2 is bound to $T_2$, and $T_1$ and $T_2$ are connected to each other by L.

2. The method according to claim 1, further comprising adding a second linker molecule (1) that connects $FE_1$ or $FE_2$, with $BE_1$ or $BE_2$ into steps i) to iv) such that, in said biomolecular complex, each of $FE_1$ and $FE_2$ are attached to one of $BE_1$ and $BE_2$ through 1.

3. The method according to claim 2, wherein 1 is a nucleic acid polymer having a pre-determined physical property.

4. The method according to claim 1, further comprising performing steps i)-iv) using functional elements other than $FE_1$ and $FE_2$, and binding elements other than $BE_1$ and $BE_2$, and forming a library of separate stock solutions.

5. A method for the production of a library comprising different biomolecular complexes, said method comprising:
   (a) providing separate solutions of different first functional elements, each first functional element ($FE_1$) from said first functional elements adapted to specifically attach to a first binding element ($BE_1$), and $BE_1$ adapted to specifically attach to a first target molecule or area ($T_1$),
   (b) providing separate solutions of different second functional elements, each second functional element ($FE_2$) from said second functional elements adapted to specifically attach to a second binding element ($BE_2$), and $BE_2$ adapted to specifically attach to a second target molecule or area ($T_2$),
   (c) providing separate solutions of said binding elements $BE_1$ and $BE_2$, each of $BE_1$ and $BE_2$ comprising a nucleotide sequence or peptide nucleic acid (PNA) sequence,
   (d) providing separate solutions of linker molecules, each linker molecule (L) from said linker molecules comprising a nucleic acid molecule having a distinct physical property,
   (e) reacting one $FE_1$ from said first functional elements of step (a) with one of $BE_1$ and $BE_2$ of step (c) and forming a complex $FE_1$-$BE_1$ or $FE_1$-$BE_2$,
   (f) reacting one FE2 from said second functional elements of step (b) with one of $BE_1$ and $BE_2$ of step (c), different from the binding element used in step (e), and forming a complex $FE_2$-$BE_2$ or $FE_2$-$BE_1$,
   (g) performing steps (e) and (f) using each of said first functional elements and said second functional elements and forming different $FE_1$-$BE_1$ or $FE_1$-$BE_2$ and different $FE_2$-$BE_2$ or $FE_2$-$BE_1$,
   (h) reacting each linker molecule L from said linker molecules from step (d) with $T_1$ and $T_2$ and forming $T_1$-L-$T_2$, $T_1$ comprising a target sequence capable of specific binding to $BE_1$ and $T_2$ comprising a target sequence capable of specific binding to $BE_2$,
   (i) reacting $FE_1$-$BE_1$ or $FE_1$-BE2 and FE2-BE2 or FE2-BE1 of steps (e) and (f) with $T_1$-L-$T_2$ and producing a biomolecular complex wherein said biomolecular complex is and (j) performing steps (h) and (i) using said different $FE_1$-$BE_1$ or $FE_1$-$BE_2$ and said different $FE_2$-$BE_2$ or $FE_2$-$BE1$ from step (g) and producing a library of different biomolecular complexes, wherein, in each of said different biomolecular complexes, each of $FE_1$ and $FE_2$ is attached to one of $BE_1$ and $BE_2$, $BE_1$ is bound to $T_1$ and BE2 is bound to $T_2$, and $T_1$ and $T_2$ are connected to each other by L.

6. The method according to claim 5, wherein L further comprises a marker or label chosen among a reporter gene, a radioactive label, and a fluorescent label.

7. The method according to claim 5, wherein $FE_1$ and $FE_2$ are chosen among a natural or synthetic peptide, a lipid, a glycoprotein, a receptor ligand, and a fraction thereof.

8. The method according to claim 5, further comprising adding a second linker molecule (1) into one of steps e) and f) such that, in each of said different biomolecular complexes, each of $FE_1$ and $FE_2$ is attached to BE1 or BE2 through 1.

9. The method according to claim 8, wherein 1 is a nucleic acid polymer having a pre-determined physical property.

* * * * *